United States Patent [19]
Gradeff

[11] 3,971,830
[45] July 27, 1976

[54] PROCESS FOR THE SEMIHYDROGENATION OF CITRAL TO CITRONELLAL

[75] Inventor: Peter S. Gradeff, Andover, N.J.

[73] Assignee: Rhodia, Inc., New York, N.Y.

[22] Filed: Mar. 24, 1975

[21] Appl. No.: 561,469

Related U.S. Application Data

[63] Continuation-in-part of Ser. No. 211,794, Dec. 23, 1971, abandoned.

[52] U.S. Cl. .............................................. 260/601 R
[51] Int. Cl.² ........................................ C07C 47/20
[58] Field of Search ................. 260/601 R; 211/794

[56] References Cited
UNITED STATES PATENTS 1,210,681   1/1917   Paal ............................... 260/601 R
3,280,192   10/1966   Levy et al. ...................... 260/601 R

OTHER PUBLICATIONS

Clark, N. G., Modern Org. Chem., pp. 232, 233, 238 and 239, 1964, Oxford Press.

Primary Examiner—James O. Thomas, Jr.
Assistant Examiner—W. B. Lone

[57] ABSTRACT

A process is provided for the semihydrogenation of the olefinic group in conjugated position to a carbonyl group in citral, a dienic aldehyde. The dienic aldehyde is hydrogenated with hydrogen in the presence of a palladium catalyst, a lower aliphatic alcohol, and an aqueous alkaline solution. The process is of particular application to the semihydrogenation of citral to citronellal.

14 Claims, No Drawings

PROCESS FOR THE SEMIHYDROGENATION OF CITRAL TO CITRONELLAL

This application is a continuation-in-part of Ser. No. 211,794, filed Dec. 23, 1971, and now abandoned.

Citral, 3,7-dimethyl-2-6-octadiene-al, is a constituent of oil of lemon grass, and it is also present, to a limited extent, in oils of verbena, lemon, and orange. Until recently, this supply has also been dependent upon the availability of these oils. However, in recent years, syntheses have been developed which make it possible to prepare citral synthetically in a high purity. Citral has two ethylenic groups in nonconjugated positions and a carbonyl group in conjugated position to the 6-ethylenic group. As a result, the semihydrogenation of citral to 3,7-dimethyl-6-octen-al in good yield has proved difficult, and no method is at present available which is capable of producing sufficiently pure citronellal in good yield and sufficiently economically to warrant its use commercially.

For example, it has been reported (*J. Applied Chem. USSR* 10, 119-25) that hydrogenation of citral can result in a 64% yield of citronellal, but such a yield is certainly unsatisfactory for use commercially. One of the problems is that the aldehyde group is sensitive and tends to be reduced to the alcohol. Moreover, the 6-ethylenic group can also be hydrogenated. This group is present in an aliphatic chain and as such is available for attack.

In this respect, the semihydrogenation of citral differs from the hydrogenation of conjugated aromatic aldehydes such as cinnamic aldehydes in which the ethylenic double bond in the side chain is conjugated with the carbonyl group and also with the aromatic conjugation of the benzene ring. Levy and Friedman, U.S. Pat. No. 3,280,192, patented Oct. 18, 1966, discuss the problems that arise in this connection. They point out that the selective reduction of an olefinic linkage in the presence of a readily reducible group such as an aldehyde function usually cannot be achieved directly, and the catalytic hydrogenation of cinnamic aldehyde results in a variety of products and mixtures of products, of which the dihydrocinnamic aldehydes are only one component, including as well cinnamic alcohol, dihydrocinnamic alcohol and dihydrocinnamic aldehyde. Levy and Friedman found that a highly selective hydrogenation of the double bond of cinnamic aldehyde and its lower alkyl substituted derivatives could be effected by employing palladium and an aqueous alkaline reaction medium for the hydrogenation. When such a combination is used, the hydrogenation proceeds with substantially no formation of the undesirable alcohol by-product, and the process finds an automatic end point in that the absorption of hydrogen ceases when only the olefinic double bond is saturated. However, Levy and Friedman do not indicate that the process is applicable to conjugated olefinic aldehydes containing a second nonconjugated ethylenic group, but confine their description to aromatic aldehydes of the type of cinnamic aldehyde. They also point out that when a one-phase alcohol solution is used in their process, mixtures of the possible reaction products or, in some cases, the olefinic alcohol, are obtained, and consequently they require that the aqueous alkaline medium be present in a separate phase from the cinnamic aldehyde, and an alcohol is not present. The data in Table I shows, for instance, that the reduction with platinum oxide of p-tertiary-butyl-alpha-methylcinnamic aldehyde in ethanol containing 0.2% sodium hydroxide gives a negligible yield of dihydrocinnamic aldehyde, and mostly cinnamic alcohol, confirming the necessity of avoiding a one-phase alcohol solution for the reaction.

Levy and Friedman in British Pat. No. 1,086,447, published Oct. 11, 1967, extend the disclosure of U.S. Pat. No. 3,280,192, somewhat, and indicate that citronellal can be hydrogenated to citronellol in their process, at 50° to 80°C., using aqueous sodium carbonate solution and palladium on charcoal, in a 93.5% yield. This suggests that the aldehyde group of citronellal is not stable under their reaction conditions, even in the absence of the alcohol solvent (in the presence of which they had indicated in U.S. Pat. No. 3,280,192, cinnamic aldehyde is converted to an alcohol), whereas the olefinic group is stable.

Givaudan Offenlegungschrift No. 2,114,211, published Oct. 14, 1971, and Easter et al. U.S. Pat. No. 3,860,657, patented Jan. 14, 1975, describe the hydrogenation of citral in good yield, with very little unconverted citral, very little dimethyl octanal, and practically no citronellol, isopulegol or dimethyl octanol, by using a palladium catalyst in the presence of a small amount of water and a base. Strong, moderately strong, and weak bases can be used, as well as organic amines. In the Examples, however, no yield data are given, merely the analysis of the composition of the product by vapor phase chromatography, which gives no indication of the amount of polymer or other nonvolatile residue formed.

In accordance with the instant invention, a process is provided for the selective hydrogenation of the olefinic group in a conjugated position to the carbonyl group in citral and homologous dienic aldehydes, accomplished in the presence of a palladium catalyst and hydrogen gas in alkaline alcoholic reaction medium. The reaction proceeds at room temperature and at atmospheric pressure, although lower or higher temperatures and higher pressures can be used, if desired. The dienic aldehyde is present in the same aqueous phase as the alcohol and the alkali; water can be present in the same or in a separate phase, according to the relative amounts of water and alcohol present.

The process of the invention is applicable to citral and to homologous dienic aldehydes, having the formula:

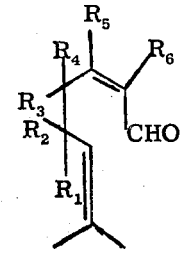

wherein $R_1$, $R_2$, $R_3$, $R_4$, and $R_6$ are selected from the group consisting of hydrogen and lower alkyl groups having from one to about five carbon atoms and $R_5$ is a lower alkyl group having from one to about five carbon atoms. The R alkyl groups can be straight chain or branched chain.

Exemplary R alkyl groups include methyl, ethyl, propyl, isopropyl, butyl, sec-butyl, tert-butyl, isobutyl, amyl, isoamyl, and tert-amyl.

The process of the invention is of particular application to citral 3,7-dimethyl-2,6-octadiene-al which can be converted to citronellal in yields in excess of 95%. In the case of citral, the reaction proceeds as follows:

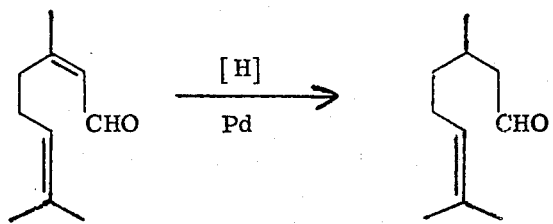

The process is applicable to both geometric isomers of citral, geranial and neral, as well as to the lower alkyl homologues of citral.

Other aldehydes to which the invention is applicable include:
3-ethyl-7-methyl-2,6-octadiene-al
3-isobutyl-7-methyl-2,6-octadiene-al
3-amyl-7-methyl-2,6-octadiene-al
2,3,4,5,7-pentamethyl-2,6-octadiene-al
3,5,7-trimethyl-2,6-octadiene-al
3,4,4,5,5,7-hexamethyl-2,6-octadiene-al
2,4,7-trimethyl-3-isopropyl-2,6-octadiene-al
2,3,7-trimethyl-2,6-octadiene-al It is essential that the hydrogenation be carried out in the presence of a lower aliphatic alcohol having from one to about five carbon atoms, such as methanol, ethanol, propanol, isopropanol, butanol, 2-butanol, tert-butanol, and isobutanol. In the absence of the alcohol, the reaction proceeds rather slowly and a considerable amount of high polymeric residue is formed, selectivity is considerably reduced, and the yield is low.

In the absence of the alcohol, and with base and water present, the reaction proceeds slowly, and may stop short of completion. For instance, when the amount of catalyst is within the range from 0.32 to 0.82 g per 100 g citral, the reaction stops at from 25 to 30% short of completion. The reaction rate is also accelerated when the amount of catalyst is almost tripled. In this case, however, the reaction is not selective and amounts of the order of 10% and more tetrahydrocitronellal are produced.

Consequently, the addition of alcohol improves reaction rate and the purity of the product and the selectivity. Most importantly, since the alcohol increases the reaction rate considerably, it makes it possible to reduce the amount of catalyst to a very small amount, as little as 0.001 gram of palladium metal per 100 g of citral, on a suitable support. In addition, the smaller amount of catalyst reduces the amount of isopulegol formed, and is economically advantageous.

Usually, an amount of alcohol at least about 10% by weight of the dienic aldehyde increases reaction rate satisfactorily. There is no upper limit on the amount and since the alcohol can serve as a solvent, it can be present in a considerable excess. If it is, a single-phase reaction system can be obtained, even in the presence of large amounts of water. However, unduly dilute solutions increase handling difficulties, because of the greater volumes of material, and are not normally practical. Consequently, the amount of alcohol is usually not in excess of about 200% and preferably is not in excess of about 100% by weight of the dienic aldehyde.

If the reaction is carried out solely in the presence of the alcohol, a considerable proportion of the starting material may be converted to the saturated aldehyde, resulting in a reduced yield. The addition of alkali and water reduces any tendency to hydrogenate the 2-double bond, and also increases the reaction rate. The addition of alkali should be in an amount of at least about 0.05% by weight of the dienic aldehyde. Larger amounts of alkali can be used, especially in the case of weak bases, but the amount of alkali should not be unduly high, in order to avoid undesirable side reactions. Normally, therefore, the amount of alkali is not in excess of about 5%, and preferably from about 0.1 to about 3%.

The alkali can be any inorganic or organic base or alkaline salt. Strong and weak alkali can be used. Strong inorganic alkali metal and alkaline earth metal hydroxides which can be used include sodium hydroxide, potassium hydroxide, lithium hydroxide, and barium hydroxide. Also useful are alkaline-reacting alkali metal and alkaline earth metal salts, such as sodium carbonate and potassium carbonate. Weak alkaline-reacting alkali metal and alkaline earth metal salts include sodium and potassium borate, sodium and potassium acetate, calcium and barium acetate, and calcium and barium formate.

The alkali can also be an organic amine which is nonreactive and soluble in the reaction mixture, and which preferably, although not necessarily, is tertiary. Exemplary are monoethanolamine, diethanolamine, triethanolamine, mono-, di-, and tri-tert-butyl amine, tri-isobutyl amine, dihexylamine, trimethyl amine, triethylamine, piperidine, pyridine, pyridine, pyrrole, morpholine, triamyl amine, monooctylamine, dipropylamine, diphenylamine, dibenzylamine toluidine, triphenylamine, aniline, and cyclohexylamine.

The alkali should be in solution in the reaction mixture, either in alcohol or in water, which may be present as a separate phase. If some of the alkali is in solution, excess alkali which is undissolved can also be present.

The alkali can be brought partly into solution in the alcohol and partly in solution in a small amount of water, thereby producing as one phase an alkaline aqueous alcoholic solution containing the alkali and the dienic aldehyde, and aqueous alkali as the other phase. Water has a beneficial effect, even if it is present in large amounts, and may result in the formation of a two-phase system. The amount of water is normally within the range from about 0.1 to about 200%, and preferably from about 25 to about 125%, by weight of the dienic aldehyde.

When water alone is used, a considerable amount of polymerized viscous material is formed. Thus, water cannot really be employed in the absence of alkali, and in the absence of alcohol.

As the hydrogenation catalyst, palladium in any form can be used, but preferably the palladium is supported on a suitable inert carrier such as charcoal, alumina, barium carbonate, aluminum sulfate, carbon, or silica gel. The palladium metal is preferably in finely divided form.

The amount of palladium required is quite small; as little as 0.001 gram of palladium metal per 100 g of the dienic aldehyde is satisfactory. Amounts of up to about 1 g of palladium metal per 100 g can be used, but amounts larger than this, although satisfactory, are uneconomic, and would not therefore be employed. Preferably, the amount is within the range from about 0.005 g to about 0.1 g per 100 g of dienic aldehyde.

The starting materials, i.e., the dienic aldehyde, alcohol, alkali, and catalyst and any water, are mixed in a hydrogenation apparatus, and hydrogen then introduced until a hydrogen atmosphere is obtained, at atmospheric pressure or at elevated pressure, preferably ranging from about 5 psi to about 30 psi. Pressures up to 500 psi can be used, if desired. The reaction mixture is then agitated under hydrogen until the desired amount of hydrogen is taken up, at which time the hydrogenation of the olefinic group in a conjugated position to the carbonyl group has been substantially completed. The catalyst can then be removed, and the semihydrogenated reaction product used as is or purified by distillation.

The reaction can be carried out at from about 5°C to about room temperature, but is faster at elevated temperatures. There is no upper limit on reaction temperature, except that imposed by the stability of the dienic aldehyde and/or the olefinic aldehyde reaction product. Temperatures from about 20° up to about 100°C. are preferred, but the reaction temperature may in some cases be as high as 200°C.

The reaction proceeds rather rapidly, depending upon temperature, hydrogen concentration, and catalyst concentration. Usually, the reaction does not require more than twenty hours for completion, and may be complete in as little as one-half hour.

The following Examples in the opinion of the inventors represent preferred embodiments of the invention.

EXAMPLES 1 TO 7

The ingredients indicated in the Table below were charged in a pressure reactor. The air was displaced with nitrogen; then a hydrogen atmosphere established, and the reactor connected to the hydrogen tank at 25 psi. The reaction began upon starting the agitation. The reaction was allowed to proceed at room temperature, ranging from 20° to 25°C., for the time indicated in the Table.

In reactions which went to completion (Examples 8 to 13), as well as in Examples 6 and 7, the crude product after filtration of the catalyst was distilled, and the distillate submitted to vapor phase chromatographic (VPC) analysis, using the following conditions:

GLC: CONDITIONS FOR CITRONELLAL:

Instrument: H&P 7620A
Column: 10 foot by ⅛ inch stainless steel packed with 15% Ucon W-98 on 80 to 100 mesh Gas Chrom Q.
Oven Temp.: 100°–175°C.
Block Temp.: 270°C.
Inj. Port Temp.: 225°C.
Flow Rate: 40 ml/min. of helium
Sample size: 1 μl
Chart Speed: 0.2 in./min.
Linear Program Rate: 2°C./min.
Yield when calculated on the basis of the analysis of distilled material.

TABLE I

| Example No. | Citral Synthetic (g) | Water (g) | Base (g) | Alcohol (cc) | Catalyst g 5% Pd/C dry | PSI Range | Temp. °C. | Time Hrs. | Hydrogen Time Absorbed Hrs. % Theory | Yield % Citronellal | Yield % Tetrahydro Citronellal | Remarks |
|---|---|---|---|---|---|---|---|---|---|---|---|---|
| Control A | 33.5 | 50 | 0.5 Na₂CO₃ | — | 0.75 | 20–10 | 20–25 | 4½ | 100 | 87 | 10 | No residue or other by-products. |
| B | 30.5 | 30 | 0.3 Na₂CO₃ | — | 0.25 | 25–10 | 20–25 | 13 | 75 | | | Absorption of hydrogen stops before completion. Residual mass not distilled |
| C | 30.5 | 15 | 1.5 Na₂CO₃ | — | 0.1 | 25–10 | 20–25 | 20 | 70 | | | Same as above. |
| D | 30.5 | 5 | 0.05 Na₂CO₃ | — | 0.75 | 20–10 | 20–25 | 17 | 70 | | | Same as above |
| E | 30.5 | 0.25 | — | — | 0.25 | 25–20 | 20–25 | 6 | 45 | | | Same as above. |
| F | 30.5 | 50 | — | — | 0.75 | 20–10 | 20–25 | 6 | 90 | | | Reaction mass consists of viscous polymer-like material. |
| G | 30.5 | 50 | — | — | 0.75 | 20–10 | 20–25 | 4 | 90 | | | Confirmation of previous result. |
| 1 | 30.5 | 15 | 0.75 Na₂CO₃ | 15 cc Ethanol | 0.25 | 25–10 | 20–25 | 2½ | 105 | 94 | 4.5 | |
| 2 | 30.5 | 15 | 0.75 Na₂CO₃ | 15 cc Ethanol | 0.15 | 25–10 | 20–25 | 6 | 100 | 95 | 3.5 | |
| 3 | 30.5 | 15 | 0.75 Na₂CO₃ | 15 cc Ethanol | 0.10 | 25–10 | 20–25 | 7 | 100 | 96 | 2.5 | |
| 4 | 30.5 | 15 | 0.75 Na₂CO₃ | 15 cc Ethanol | 0.10 | Below 3 psi | 20–25 | 36 | 90 | 90 | 1.0 | Impractical to run at pressures below 5 psi. |
| 5 | 30.5 | 15 | 0.15 Ba(OH)₂ 8H₂O | 15 cc Ethanol | 0.05 | 25–10 | 20–25 | 7 | 100 | 97 | 2.0 | |
| 6 | 30.5 | 15 | 0.15 Ba(OH)₂ 8H₂O | 15 cc Methanol | 0.05 | 25–10 | 20–25 | 8 | 100 | 96 | 2.5 | |
| 7 | 30.5 | 12 | 2.0 Trimethyl amine | 15 cc Ethanol | 0.2 | 26–12 | 20–25 | 13 | 100 | 95 | 3.8 | |

It is apparent from the data for Examples 1 to 7 that in the presence of alcohol, water and alkali the yield of citronellal is good (90 to 97%), and selectivity is also good (1 to 4.5% tetrahydrocitronellal). Controls A to D show that Pd catalyst, water and alkali are not satisfactory. In Control A, 10% tetrahydro-citronellal is formed, showing selectivity is not good. In Controls B to D, the reaction is slow, and stops at from 30 to 55% short of completion. Controls E to G show that water alone is not satisfactory. There is a nearly complete absorption of hydrogen but only a polymer is obtained and no citronellal. Thus, alcohol, water and alkali together are required for good selectivity and good yields of citronellal the yield of tetrahydro-citronellal being reduced to as little as 1%, and the yield of citronellal reaching 94 to 97%. Example 7 confirms the effectiveness of organic amines as the alkali.

EXAMPLE 8

The ingredients indicated in the Table below were charged in a water-cooled pressure reactor. The air was displaced with nitrogen; then a hydrogen atmosphere established, and the reactor connected to the hydrogen tank at 115 psi. The temperature was then brought to 11°C, and the reaction began upon starting the agitation. The reaction was allowed to proceed at 11°C for a total of 22 hours.

Samples were taken at the times indicated in the Table. The crude sample after filtration of the catalyst was analysed by gas-liquid chromatographic analysis, using the conditions of Examples 1 to 7. The results obtained are shown in the Table.

TABLE II

| Synthetic Citral (95.44%) | 152.2 g | (1.0 mole) |
|---|---|---|
| MeOH | 232.8 g | |
| $H_2O$ | 1.2 g | |
| Borax (10% solution in MeOH) | 9.0 g | |
| Catalyst (5% Pd/C containing 50% $H_2O$) | 0.84 g | |

| Time Hours | $H_2$ Pressure (PSI) | Temp. (°C.) | Sample No. | % Citronellal | % Citral | % Tetrahydro-Citronellal |
|---|---|---|---|---|---|---|
| 0 | 115 | 11.1 | | | | |
| 1 | 108 | 11.1 | | | | |
| 4 | 105 | 11.2 | 1 | 12.2 | 82.2 | 1.2 |
| 6 | 105 | 11.1 | 2 | 33.1 | 60.0 | 2.4 |
| 22 | 105 | 11.1 | 3 | 76.9 | 18.7 | 4.3 |

It is apparent that the reaction proceeds slowly but in good yield at low temperature and at high pressure.

Having regard to the foregoing disclosure, the following is claimed as the inventive and patentable embodiments thereof:

1. In the process for the selective hydrogenation of the olefinic group in a conjugated position to the carbonyl group in dienic aldehydes having the formula:

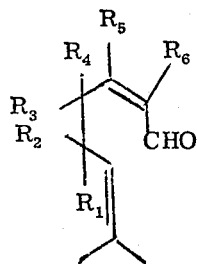

wherein $R_1$, $R_2$, $R_3$, $R_4$, and $R_6$ are selected from the group consisting of hydrogen and lower alkyl groups having from one to about five carbon atoms and $R_5$ is a lower alkyl group having from one to about five carbon atoms, which comprises hydrogenating the dienic aldehyde in the presence of a palladium metal catalyst, alkali, and water, the improvement which comprises carrying out the hydrogenation at a temperature within the range from about 5° to about 200°C, and at a pressure within the range from atmospheric pressure to about 500 psi, in the presence of a palladium metal catalyst in an amount within the range from about 0.001 g to about 1 g of palladium metal per 100 g of dienic aldehyde with a lower alkanol having from one to about five carbon atoms in a liquid aqueous alkaline reaction medium, the alkali being in an amount within the range from about 0.05 to about 5% by weight of the dienic aldehyde, and the alkanol being in an amount within the range from about 10 to about 200% by weight of the dienic aldehyde.

2. The process of claim 1 in which the aldehyde is citral, 3,7-dimethyl-2,6-octadiene-al, which is converted to citronellal.

3. The process of claim 1 in which the aldehyde is selected from the group consisting of:
3-ethyl-7-methyl-2,6-octadiene-al
3-isobutyl-7-methyl-2,6-octadiene-al
3-amyl-7-methyl-2,6-octadiene-al
2,3,4,5,7-pentamethyl-2,6-octadiene-al
3,5,7-trimethyl-2,6-octadiene-al
3,4,4,5,5,7-hexamethyl-2,6-octadiene-al
2,4,7-trimethyl-3-isopropyl-2,6-octadiene-al
2,3,7-trimethyl-2,6-octadiene-al 4. The process of claim 1 in which the alcohol is a water-soluble alcohol selected from the group consisting of methanol, ethanol, propanol, isopropanol, butanol, 2-butanol, tert-butanol, and isobutanol.

5. The process of claim 1 in which the amount of alcohol is at least about 10 up to about 100% by weight of the dienic aldehyde.

6. The process of claim 1 in which the amount of alkali is at least about 0.1 up to about 5% by weight of the dienic aldehyde.

7. The process of claim 6 in which the alkali is selected from the group consisting of alkali metal and the alkaline earth metal hydroxides.

8. The process of claim 6 in which the alkali is an organic amine.

9. The process of claim 1 in which the alkaline alcoholic reaction medium comprises water in an amount within the range from about 0.1 to about 200% by weight of the alcohol.

10. The process of claim 1 in which the palladium is supported on an inert carrier.

11. The process of claim 1 in which the amount of palladium is within the range from about 0.005 g to about 0.1 g palladium metal per 100 g of dienic aldehyde.

12. The process of claim 1 in which the hydrogen is at a pressure within the range from atmospheric pressure up to about 30 psi.

13. The process of claim 1 in which the reaction mixture is then agitated under a hydrogen atmosphere until absorption of hydrogen ceases, and the hydrogenation of the olefinic group in a conjugated position to the carbonyl group has been substantially completed, the catalyst is removed, and the semihydrogenated reaction product recovered.

14. The process of claim 1 in which the reaction is carried out at a temperature within the range from about 5° and about 100°C.

* * * * *